(12) United States Patent
Cheng et al.

(10) Patent No.: US 6,495,162 B2
(45) Date of Patent: Dec. 17, 2002

(54) CONTROLLED RELEASE ORAL TABLET HAVING A UNITARY CORE

(75) Inventors: Xiu Xiu Cheng, Davie, FL (US); Chih-Ming Chen, Davie, FL (US); Steve Jan, Coral Springs, FL (US); Joseph Chou, Coral Springs, FL (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 0 days.

(21) Appl. No.: 10/016,556

(22) Filed: Nov. 1, 2001

(65) Prior Publication Data

US 2002/0064556 A1 May 30, 2002

Related U.S. Application Data

(63) Continuation of application No. 09/594,637, filed on Jun. 15, 2000, now abandoned, which is a continuation of application No. 09/045,330, filed on Mar. 20, 1998, now Pat. No. 6,099,859.

(51) Int. Cl.[7] ................................................. A61K 9/20
(52) U.S. Cl. ...................... 424/464; 424/465; 424/468; 424/473; 424/472
(58) Field of Search ................... 424/464, 488, 424/469, 468, 489, 450, 456, 465, 473, 472

(56) References Cited

U.S. PATENT DOCUMENTS

| 3,621,097 A | 11/1971 | Scott et al. |
| 3,845,770 A | 11/1974 | Theeuwes et al. |
| 3,916,899 A | 11/1975 | Theeuwes et al. |
| 3,952,741 A | 4/1976 | Baker |
| 3,957,853 A | 5/1976 | Bohoun |
| 4,017,539 A | 4/1977 | Bosies et al. |
| 4,034,758 A | 7/1977 | Theeuwes |

(List continued on next page.)

FOREIGN PATENT DOCUMENTS

| DE | 2124256 | 11/1972 |
| EP | 0283369 | 8/1993 |
| GB | 1552179 | 9/1979 |
| WO | WO9608243 | 3/1996 |
| WO | WO9640080 | 12/1996 |
| WO | WO9717975 | 5/1997 |
| WO | WO9810786 | 3/1998 |
| WO | WO9827982 | 7/1998 |
| WO | WO9903477 | 1/1999 |
| WO | WO9947128 | 9/1999 |

OTHER PUBLICATIONS

1996 Physician Desk Reference pp. 752–757.

Primary Examiner—Thurman K. Page
Assistant Examiner—Blessing Fubara
(74) Attorney, Agent, or Firm—Hedman & Costigan, P.C.

(57) ABSTRACT

A controlled release antihyperglycemic tablet that does not contain an expanding polymer and comprising a core containing the antihyperglycemic drug, a semipermeable membrane coating the core and at least one passageway in the membrane.

47 Claims, 8 Drawing Sheets

U.S. PATENT DOCUMENTS

| | | | |
|---|---|---|---|
| 4,077,407 A | 3/1978 | Theeuwes et al. |
| 4,080,472 A | 3/1978 | Bohoun |
| 4,327,725 A | 5/1982 | Cortese et al. |
| 4,522,625 A | 6/1985 | Edgren |
| 4,587,117 A | 5/1986 | Edgren et al. |
| 4,609,374 A | 9/1986 | Ayer |
| 4,612,008 A | 9/1986 | Wong et al. |
| 4,615,698 A | 10/1986 | Guittard et al. |
| 4,624,847 A | 11/1986 | Ayer et al. |
| 4,627,850 A | 12/1986 | Deters et al. |
| 4,652,441 A | 3/1987 | Okada et al. |
| 4,673,405 A | 6/1987 | Guittard et al. |
| 4,692,336 A | 9/1987 | Eckenhoff et al. |
| 4,696,815 A | 9/1987 | Schepky et al. |
| 4,704,118 A | 11/1987 | Eckenhoff |
| 4,708,868 A | 11/1987 | Brickl et al. |
| 4,711,782 A | 12/1987 | Okada et al. |
| 4,765,989 A | 8/1988 | Wong et al. |
| 4,777,049 A | 10/1988 | Magruder et al. |
| 4,783,337 A | 11/1988 | Wong et al. |
| 4,803,076 A | 2/1989 | Ranade |
| 4,828,836 A | 5/1989 | Elger et al. |
| 4,834,985 A | 5/1989 | Elger et al. |
| 4,849,227 A | 7/1989 | Cho |
| 4,851,229 A | 7/1989 | Magruder et al. |
| 4,851,232 A | 7/1989 | Urquhart et al. |
| 4,863,724 A | 9/1989 | Schepky et al. |
| 4,865,598 A | 9/1989 | Eckenhoff |
| 4,871,549 A | 10/1989 | Ueda et al. |
| 4,892,739 A | 1/1990 | Shah et al. |
| 4,917,893 A | 4/1990 | Okada et al. |
| 4,954,298 A | 9/1990 | Yamamoto et al. |
| 4,963,141 A | 10/1990 | Eckenhoff |
| 5,024,843 A | 6/1991 | Kuczynski et al. |
| 5,028,434 A | 7/1991 | Barclay et al. |
| 5,030,452 A | 7/1991 | Curatolo |
| 5,055,306 A | 10/1991 | Barry et al. |
| 5,071,607 A | 12/1991 | Ayer et al. |
| 5,082,668 A | 1/1992 | Wong et al. |
| 5,091,190 A | 2/1992 | Kuczynski et al. |
| 5,108,756 A | 4/1992 | Curatolo |
| 5,110,597 A | 5/1992 | Wong et al. |
| 5,120,548 A | 6/1992 | McClelland et al. |
| 5,141,752 A | 8/1992 | Ayer et al. |
| 5,178,867 A | 1/1993 | Guittard et al. |
| 5,185,158 A | 2/1993 | Ayer et al. |
| 5,260,275 A | 11/1993 | Cooper et al. |
| 5,308,348 A | 5/1994 | Balaban et al. |
| 5,356,913 A | 10/1994 | Colca |
| 5,380,526 A | 1/1995 | Ise |
| 5,413,572 A | 5/1995 | Wong et al. |
| 5,476,663 A | 12/1995 | Okada et al. |
| 5,512,293 A | 4/1996 | Landrau et al. |
| 5,543,156 A | 8/1996 | Roorda et al. |
| 5,545,413 A | 8/1996 | Kuczynski et al. |
| 5,576,306 A | 11/1996 | Dressman et al. |
| 5,591,454 A | 1/1997 | Kuczynski et al. |
| 5,594,091 A | 1/1997 | Igari et al. |
| 5,611,971 A | 3/1997 | Maedera et al. |
| 5,614,578 A | 3/1997 | Dong et al. |
| 5,622,657 A | 4/1997 | Takada et al. |
| 5,629,319 A | 5/1997 | Luo et al. |
| 5,631,020 A | 5/1997 | Okada et al. |
| 5,631,021 A | 5/1997 | Okada et al. |
| 5,631,224 A | 5/1997 | Efendic et al. |
| 5,650,170 A | 7/1997 | Wright et al. |
| 5,665,394 A | 9/1997 | Igari et al. |
| 5,667,804 A | 9/1997 | Wong et al. |
| 5,668,117 A | 9/1997 | Shapiro |
| 5,674,900 A | 10/1997 | Ubillas et al. |
| 5,688,518 A | 11/1997 | Ayer et al. |
| 5,691,386 A | 11/1997 | Inman et al. |
| 5,716,640 A | 2/1998 | Kamei et al. |
| 5,716,976 A | 2/1998 | Bernstein |
| 5,719,188 A | 2/1998 | Colca |
| 5,723,269 A | 3/1998 | Akagi et al. |
| 5,747,527 A | 5/1998 | Inman et al. |
| 5,789,393 A | 8/1998 | Dressman et al. |
| 5,814,670 A | 9/1998 | Colca |
| 5,858,398 A | 1/1999 | Cho |
| 5,955,106 A | 9/1999 | Moeckel et al. |
| 5,965,584 A | 10/1999 | Ikeda et al. |
| 6,056,977 A * | 5/2000 | Bhagwat et al. ............ 424/488 |
| 6,086,920 A | 7/2000 | Frisbee et al. |
| 6,099,859 A * | 8/2000 | Cheng et al. ............... 424/464 |
| 6,099,862 A | 8/2000 | Chen et al. |
| 6,100,300 A | 8/2000 | Rogosky |
| 6,113,941 A | 9/2000 | Takada et al. |
| 6,117,451 A | 9/2000 | Kumar |
| 6,120,803 A | 9/2000 | Wong et al. |
| 6,150,384 A | 11/2000 | Ikeda et al. |
| 6,166,042 A | 12/2000 | Ikeda et al. |
| 6,166,043 A | 12/2000 | Ikeda et al. |
| 6,172,090 B1 | 1/2001 | Ikeda et al. |
| 6,197,340 B1 | 3/2001 | Byrd et al. |
| 6,239,153 B1 | 5/2001 | Ikeda et al. |

OTHER PUBLICATIONS

1998 Physician Desk Reference pp. 794–800, pp. 1217–1219, pp. 2182–2186.

Clin. Ther. 1996 May; 18(3); pp. 360–371, Campbell et al. Metformin: a New Oral Biguanide.

Brisco TA, et al. A Retrospective Analysis of the Efficacy and Safety of Metformin in the African–American Patient.

\* cited by examiner

US 6,495,162 B2

CONTROLLED RELEASE ORAL TABLET HAVING A UNITARY CORE

This application is a continuation of application Ser. No. 09/594,637 filed Jun. 15, 2000 now abandoned, which is a continuation of application Ser. No. 09/045,330, filed Mar. 20, 1998, now U.S. Pat. No. 6,099,859.

BACKGROUND OF THE INVENTION

The present invention relates to controlled release unit dose formulations containing an antihyperglycemic drug. More specifically, the present invention relates to an oral dosage form comprising a biguanide such as metformin or buformin or a pharmaceutically acceptable salt thereof such as metformin hydrochloride or the metformin salts described in U.S. Pat. Nos. 3,957,853 and 4,080,472 which are incorporated herein by reference.

In the prior art, many techniques have been used to provide controlled and extended-release pharmaceutical dosage forms in order to maintain therapeutic serum levels of medicaments and to minimize the effects of missed doses of drugs caused by a lack of patient compliance.

In the prior art are extended release tablets which have an osmotically active drug core surrounded by a semipermeable membrane. These tablets function by allowing a fluid such as gastric or intestinal fluid to permeate the coating membrane and dissolve the active ingredient so it can be released through a passageway in the coating membrane or if the active ingredient is insoluble in the permeating fluid, pushed through the passageway by an expanding agent such as a hydrogel. Some representative examples of these osmotic tablet systems can be found in U.S. Pat. Nos. 3,845,770, 3,916,899, 4,034,758, 4,077,407 and 4,783,337. U.S. Pat. No. 3,952,741 teaches an osmotic device wherein the active agent is released from a core surrounded by a semipermeable membrane only after sufficient pressure has developed within the membrane to burst or rupture the membrane at a weak portion of the membrane.

The basic osmotic device described in the above cited patents have been refined over time in an effort to provide greater control of the release of the active ingredient. For example U.S. Pat. Nos. 4,777,049 and 4,851,229 describe an osmotic dosage form comprising a semipermeable wall surrounding a core. The core contains an active ingredient and a modulating agent wherein the modulating agent causes the active ingredient to be released through a passageway in the semipermeable membrane in a pulsed manner. Further refinements have included modifications to the semipermeable membrane surrounding the active core such as varying the proportions of the components that form the membrane, i.e U.S. Pat. Nos. 5,178,867, 4,587,117 and 4,522,625 or increasing the number of coatings surrounding the active core, i.e U.S. Pat. Nos. 5,650,170 and 4,892,739.

Although vast amounts of research has been performed on controlled or sustained release compositions and in particular on osmotic dosage forms, very little research has been performed in the area of controlled or sustained release compositions that employ antihyperglycemic drugs.

The limited work on controlled or sustained release formulations that employ antihyperglycemic drugs such as metformin hydrochloride has been limited to the combination of the antihyperglycemic drug and an expanding or gelling agent to control the release of the drug from the dosage form. This limited research is exemplified by the teachings of WO 96/08243 and by the GLUCOPHAGE® product which is a commercially available product from Bristol-Myers Squibb Co. containing metformin HCl.

It is reported in the 50th Edition of the Physicians' Desk Reference, copyright 1996, p. 753, that food decreases the extent and slightly delays the absorption of metformin delivered by the GLUCOPHAGE® dosage form. This decrease is shown by approximately a 40% lower peak concentration and a 25% lower AUC in plasma and a 35 minute prolongation of time to peak plasma concentration following administration of a single GLUCOPHAGE® tablet containing 850 mg of metformin HCl with food compared to the similar tablet administered under fasting conditions.

It is an object of the present invention to provide a controlled or sustained release formulation for an antihyperglycemic drug wherein the bioavailability of the drug is not decreased by the presence of food.

It is a further object of the present invention to provide a controlled or sustained release formulation for an antihyperglycemic drug that does not employ an expanding polymer.

It is also a further object of the present invention to provide a controlled or sustained release formulation for an antihyperglycemic drug that can provide continuous and non-pulsating therapeutic levels of an antihyperglycemic drug to an animal or human in need of such treatment over a twelve hour to twenty-four hour period.

It is an additional object of the present invention to provide a controlled or sustained release formulation for an antihyperglycemic drug that obtains peak plasma levels approximately 8–12 hours after administration.

It is also an object of this invention to provide a controlled or sustained release pharmaceutical tablet having only a homogeneous osmotic core wherein the osmotic core component may be made using ordinary tablet compression techniques.

SUMMARY OF THE INVENTION

The foregoing objectives are met by a controlled release dosage form comprising:
(a) a core comprising:
  (i) an antihyperglycemic drug;
  (ii) optionally a binding agent; and
  (iii) optionally an absorption enhancer;
(b) a semipermeable membrane coating surrounding the core; and
(c) at least one passageway in the semipermeable membrane.

The dosage form of the present invention can provide therapeutic levels of the antihyperglycemic drug for twelve to twenty-four hour periods and does not exhibit a decrease in bioavailability if taken with food. In fact, a slight increase in the bioavailability of the antihypoglycemic drug is observed when the controlled release dosage form of the present invention is administered with food. In a preferred embodiment, the dosage form will be administered once a day, ideally with or after a meal and most preferably with or after the evening meal, and provide therapeutic levels of the drug throughout the day with peak plasma levels being obtained between 8–12 hours after administration.

DETAILED DESCRIPTION OF THE INVENTION

Figure 1:
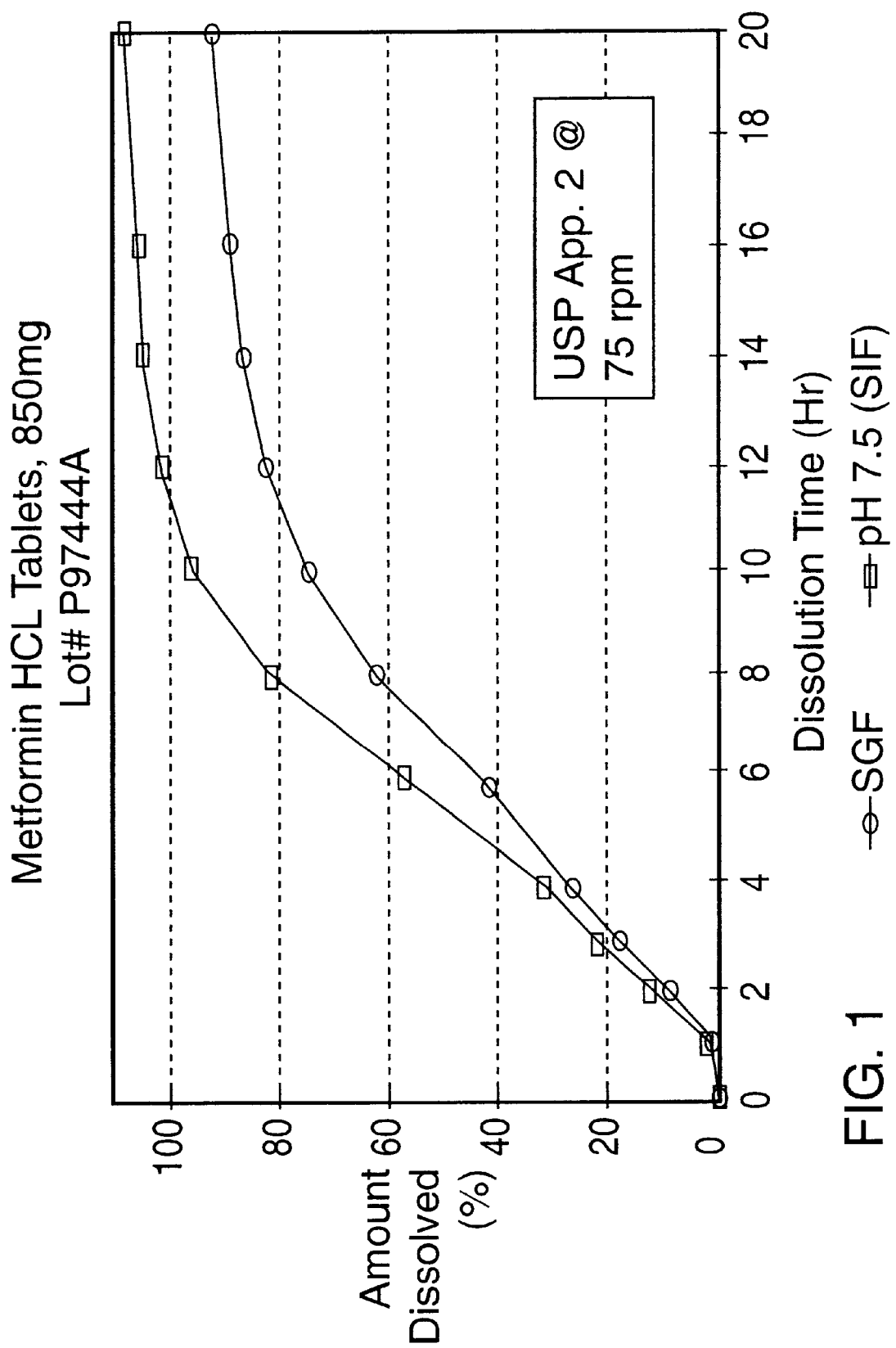
FIG. 1 is a graph which depicts the dissolution profile in simulated intestinal fluid (pH 7.5 phosphate buffer) and simulated gastric fluid (SGF) of the formulation described in Example 1 as tested according to the procedure described in United States Pharmacopeia XXIII, Apparatus 2 @ 75 rpm.

The term antihyperglycemic drugs as used in this specification refers to drugs that are useful in controlling or managing noninsulin-dependent diabetes mellitus (NIDDM). Preferably, the antihyperglycemic drug is a biguanide such as metformin or buformin or a pharmaceutically acceptable salt thereof such as metformin hydrochloride.

The binding agent may be any conventionally known pharmaceutically acceptable binder such as polyvinyl pyrrolidone, hydroxypropyl cellulose, hydroxyethyl cellulose, ethylcellulose, polymethacrylate, waxes and the like. Mixtures of the aforementioned binding agents may also be used. The preferred binding agents are water soluble such as polyvinyl pyrrolidone having a weight average molecular weight of 25,000 to 3,000,000. The binding agent comprises approximately about 0 to about 40% of the total weight of the core and preferably about 3% to about 15% of the total weight of the core.

The core may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-bis(β-aminoethyl ether)-N,N,N,N-tetraacetic acid (EGTA). The core comprises approximately 0 to about 20% of the absorption enhancer based on the total weight of the core and most preferably about 2% to about 10% of the total weight of the core.

The core of the present invention which comprises the antihyperglycemic drug, the binder which preferably is a pharmaceutically acceptable water soluble polymer and the absorption enhancer is preferably formed by wet granulating the core ingredients and compressing the granules with the addition of a lubricant into a tablet on a rotary press. The core may also be formed by dry granulating the core ingredients and compressing the granules with the addition of a lubricant into tablets or by direct compression.

Other commonly known excipients may also be included into the core such as lubricants, pigments or dyes. The homogeneous core is coated with a semipermeable membrane, preferably a modified polymeric membrane to form the controlled release tablet of the invention. The semipermeable membrane is permeable to the passage of an external fluid such as water and biological fluids and is impermeable to the passage of the antihyperglycemic drug in the core. Materials that are useful in forming the semipermeable membrane are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 4,11210 which are incorporated herein by reference. The preferred semipermeable membrane material around the core is a water insoluble cellulose derivative. The most preferred semipermeable membrane material is cellulose acetate comprising an acetyl content of 39.3 to 40.3%, commercially available from Eastman Fine Chemicals.

In an alternative embodiment, the semipermeable membrane can be formed from the above-described polymers and a flux enhancing agent. The flux enhancing agent increases the volume of fluid imbibed into the core to enable the dosage form to dispense substantially all of the antihyperglycemic drug through the passageway and/or the porous membrane. The flux enhancing agent can be a water soluble material or an enteric material. Some examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methycellulose, hydroxypropyl methycellulose phthalate, cellulose acetate phthalate, polyvinyl alcohols, methacrylic acid copolymers and mixtures thereof. The preferred flux enhancer is PEG 400.

The flux enhancer may also be a drug that is water soluble such as metformin or its pharmaceutically acceptable salts or a drug that is soluble under intestinal conditions. If the flux enhancer is a drug, the present dosage form has the added advantage of providing an immediate release of the drug which is selected as the flux enhancer.

The flux enhancing agent comprises approximately 0 to about 40% of the total weight of the coating, most preferably about 2% to about 20% of the total weight of the coating. The flux enhancing agent dissolves or leaches from the semipermeable membrane to form paths in the semipermeable membrane for the fluid to enter the core and dissolve the active ingredient.

The semipermeable membrane may also be formed with commonly known excipients such a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 2% to about 15% of the plasticizer can be used based upon the total weight of the coating.

As used herein the term passageway includes an aperture, orifice, bore, hole, weaken area or an erodible element such as a gelatin plug that erodes to form an osmotic passageway for the release of the antihyperglycemic drug from the dosage form. A detailed description of the passageway can be found in United States Patents such as U.S. Pat. Nos. 3,845,770, 3,916,899, 4,034,758, 4,077,407, 4,783,337 and 5,071,607.

Generally, the membrane coating around the core will comprise from about 1% to about 5% and preferably about 2% to about 3% based on the total weight of the core and coating.

In an alternative embodiment, the dosage form of the present invention may also comprise an effective amount of the antihyperglycemic drug that is available for immediate release. The effective amount of antihyperglycemic drug for immediate release may be coated onto the semipermeable membrane of the dosage form or it may be incorporated into the semipermeable membrane.

In a preferred embodiment the dosage form will have the following composition:

|  | Preferred | Most Preferred |
| --- | --- | --- |
| CORE: |  |  |
| drug | 50–98% | 75–95% |
| binder | 0–40% | 3–15% |
| absorption enhancer | 0–20% | 2–10% |
| COATING: |  |  |
| semipermeable polymer | 50–99% | 75–95% |
| flux enhancer | 0–40% | 2–20% |
| plasticizer | 0–25% | 2–15% |

The dosage forms prepared according to the present invention should exhibit the following dissolution profile when tested in a USP type 2 apparatus at 75 rpms in 900 ml of simulated intestinal fluid (pH 7.5 phosphate buffer) and at 37° C.:

| Time (hours) | Preferred | Most Preferred |
| --- | --- | --- |
| 2 | 0–25% | 0–15% |
| 4 | 10–45% | 20–40% |
| 8 | 30–90% | 45–90% |
| 12 | NTL 50% | NTL 60% |
| 16 | NTL 60% | NTL 70% |
| 20 | NTL 70% | NTL 80% |

NTL = NOT LESS THAN

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1995 Edition may be used to optimize the formulations of the invention.

DESCRIPTION OF THE PREFERRED EMBODIMENTS

EXAMPLE 1

A controlled release tablet containing 850 mg of metformin HCl and having the following formula is prepared as follows:

| I  Core | |
| --- | --- |
| metformin HCl | 90.54% |
| povidone[1,] USP | 4.38% |
| sodium tribasic phosphate | 4.58% |
| magnesium stearate | 0.5% |

[1]approximate molecular weight 50,000; dynamic viscosity (10% w/v solution at 20° C.) = 5.5–8.5 m Pa s.

(a) Granulation

The metformin HCl is delumped by passing it through a 40 mesh screen and collecting it in a clean, polyethylene-lined container. The povidone, K-30, and sodium tribasic phosphate are dissolved in purified water. The delumped metformin HCl is then added to a top-spray fluidized bed granulator and granulated by spraying the binding solution of povidone and sodium tribasic phosphate under the following conditions: inlet air temperature of 50–70° C.; atomization air pressure of 1–3 bars; and spray rate of 10–100 ml/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

(c) Seal Coating (optional)

The core tablet is seal coated with an opadry material or other suitable water-soluble material by first dissolving the Opadry material, preferably Opadry Clear, in purified water. The opadry solution is then sprayed onto the core tablet using a pan coater under the following conditions: exhaust air temperature of 38–42° C.; atomization pressure of 28–40 psi; and spay rate of 10–15 ml/min. The core tablet is coated with the sealing solution until a theoretical coating level of approximately 2% is obtained.

| II Sustained Release Coating | |
|---|---|
| cellulose acetate (398–10)[2] | 85% |
| triacetin | 5% |
| PEG 400 | 10% |

[2]acetyl content 39.3–40.3%

(d) Sustained Release Coating

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16–22° C.; atomization pressure of approximately 3 bars; and spray rate of 120–150 ml/min. The sealed core tablet is coated until a theoretical coating level of approximately 3% is obtained.

The resulting tablet is tested in simulated intestinal fluid (pH 7.5) and simulated gastric fluid (SGF) according to the procedure described in United States Pharmacopeia XXIII, Apparatus 2 @ 75 rpm and found to have the following release profile:

| TIME (hours) | % Released (SGF) | % Released (pH 7.5) |
|---|---|---|
| 2 | 9 | 12 |
| 4 | 27 | 32 |
| 8 | 62 | 82 |
| 12 | 82 | 100 |
| 16 | 88 | 105 |
| 20 | 92 | 108 |

The release profile in pH 7.5 and SGF of the sustained release product prepared in this Example is shown in FIG. 1.

Figure 4:
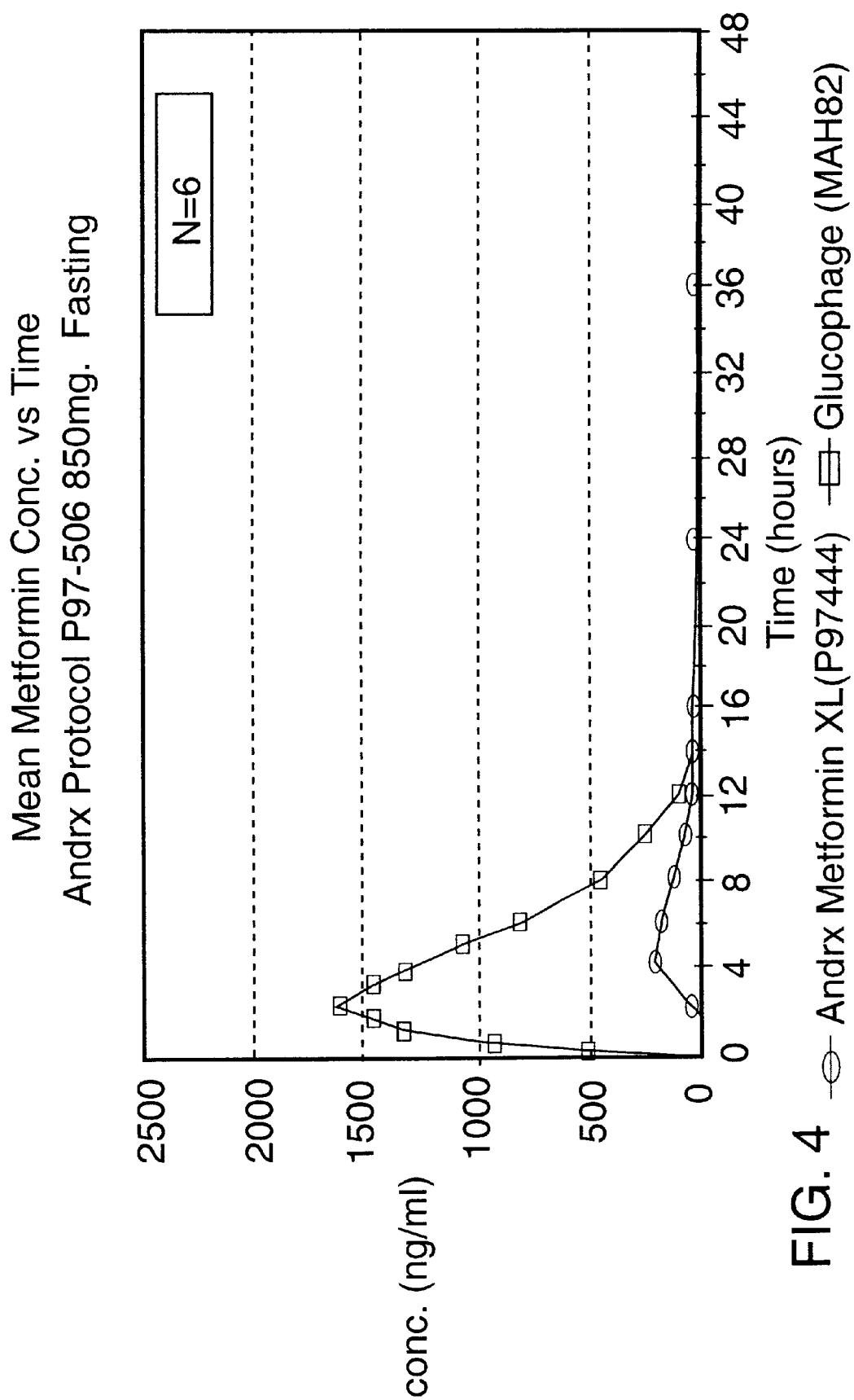
FIG. 4 is a graph depicting the in vivo metformin plasma profile of the formulation described in Example 1 and the in vivo metformin plasma profile of the commercially available metformin HCl product GLUCOPHAGE® under fasting conditions.

FIG. 4 depicts the in vivo metformin plasma profile of the sustained release product prepared in this Example. Also shown in FIG. 4 is the in vivo metformin plasma profile of GLUCOPHAGE®, a commercially available pharmaceutical product containing the drug metformin HCl.

EXAMPLE 2

A controlled release tablet containing 850 mg of metformin HCl and having the following formula is prepared as follows:

| I Core | |
|---|---|
| metformin HCl | 88.555% |
| povidone[3], USP | 6.368% |
| sodium lauryl sulfate | 4.577% |
| magnesium stearate | 0.5% |

[3]approximate molecular weight = 1,000,000, dynamic viscosity (10% w/v solution at 20° C.) = 300–700 m Pa s.

(a) Granulation

The metformin HCl and sodium lauryl sulfate are delumped by passing them through a 40 mesh screen and collecting them in a clean, polyethylene-lined container. The povidone, K-90F, is dissolved in purified water. The delumped metformin HCl and sodium lauryl sulfate are then added to a top-spray fluidized bed granulator and granulated by spraying with the binding solution of povidone under the following conditions: inlet air temperature of 50–70° C.; atomization air pressure of 1–3 bars; and spray rate of 10–100 ml/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the coated granules are compressed on a rotary press fitted with 15/32" round standard concave punches (plain lower punch, upper punch with an approximately 1 mm indentation pin).

(c) Seal Coating (optional)

The core tablet is seal coated with an Opadry material or other suitable water-soluble material by first dissolving the Opadry material, preferably Opadry Clear in purified water. The Opadry solution is then sprayed onto the core tablet using a pan coater under the following conditions: exhaust air temperature of 38–42° C.; atomization pressure of 28–40 psi; and spay rate of 10–15 ml/min. The core tablet is coated with the sealing solution until a theoretical coating level of approximately 2% is obtained.

| II Sustained Release Coating | |
|---|---|
| cellulose acetate (398–10)[4] | 85% |
| triacetin | 5% |
| PEG 400 | 10% |

[4]acetyl content 39.3–40.3%

(d) Sustained Release Coating

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16–22° C.; atomization pressure of approximately 3 bars; and spray rate of 120–150 ml/min. The sealed core tablet is coated until a theoretical coating level of approximately 3% is obtained.

The resulting tablet is tested in simulated intestinal fluid (pH 7.5) and simulated gastric fluid (SGF) according to the procedure described in United States Pharmacopeia XXIII, Apparatus 2 @ 75 rpm and found to have the following release profile:

| TIME (hours) | % Released (SGF) | % Released (pH 7.5) |
|---|---|---|
| 2 | 13 | 12 |
| 4 | 29 | 27 |
| 8 | 55 | 52 |
| 12 | 72 | 71 |
| 16 | 81 | 83 |
| 20 | 87 | 91 |

Figure 2:
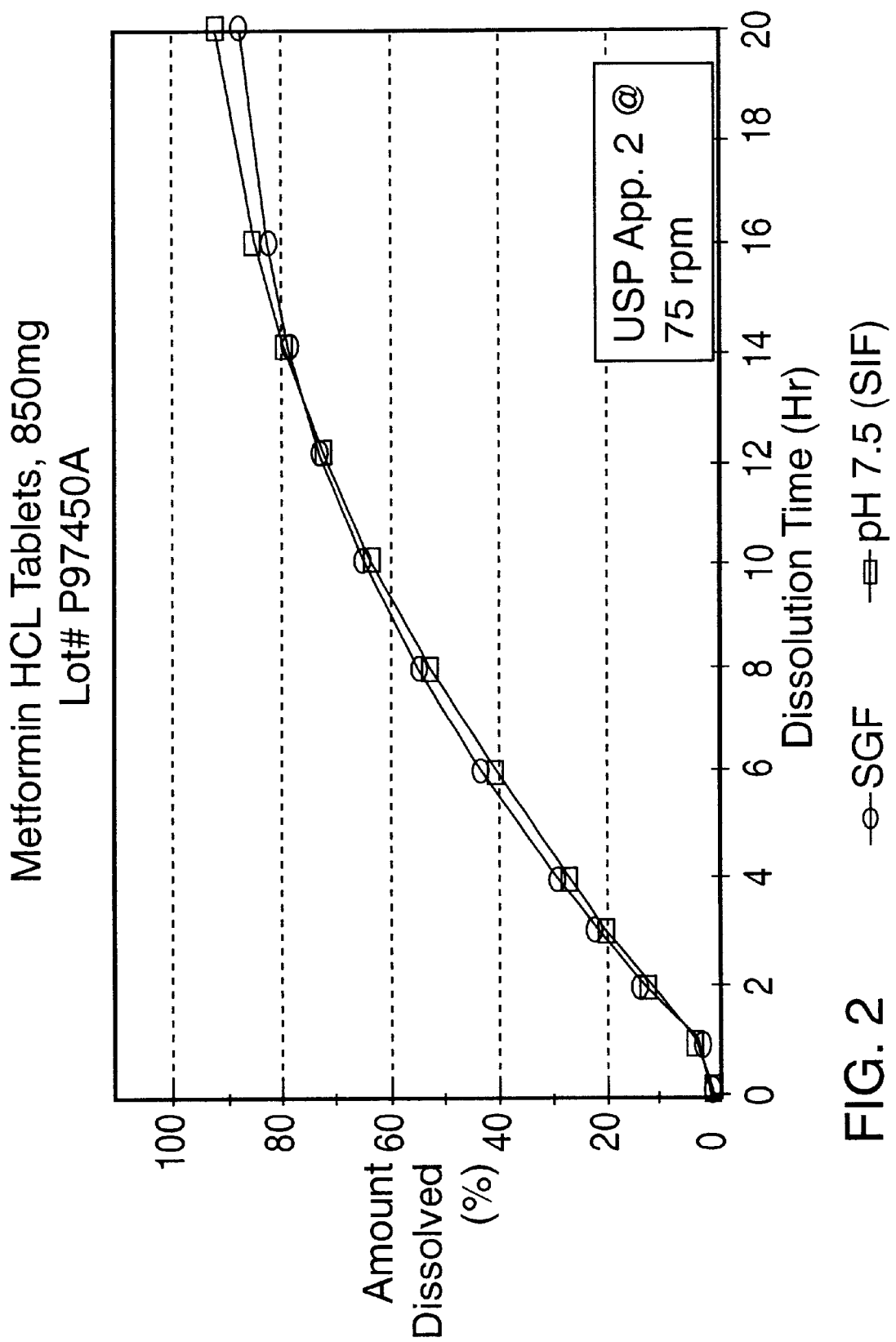
FIG. 2 is a graph which depicts the dissolution profile in simulated intestinal fluid (pH 7.5 phosphate buffer) and simulated gastric fluid (SGF) of the formulation described in Example 2 as tested according to the procedure described in United States Pharmacopeia XXIII, Apparatus 2 @ 75 rpm.

The release profile in pH 7.5 and SGF of the sustained release product prepared in this Example is shown in FIG. 2.

Figure 5:
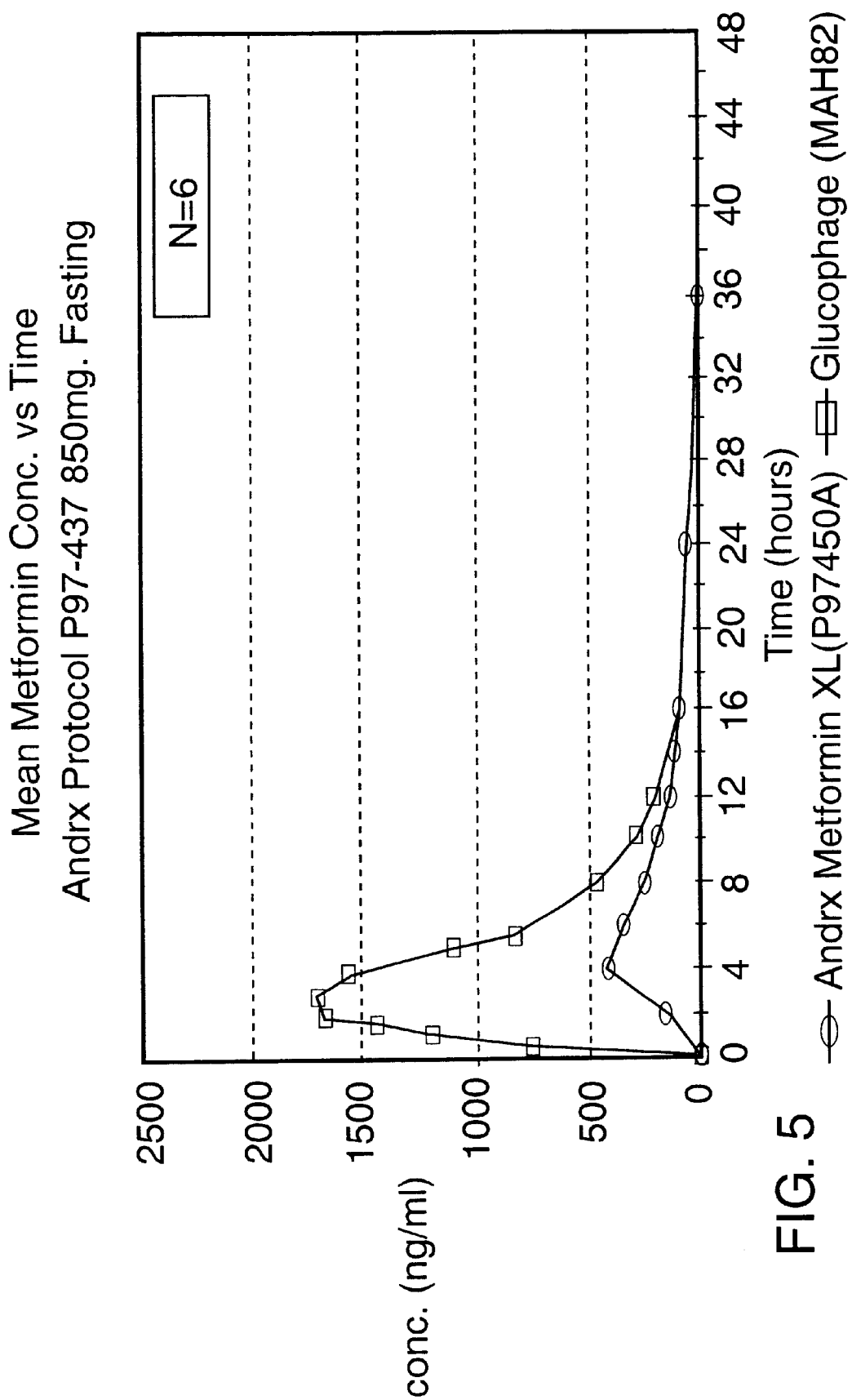
FIG. 5 is a graph depicting the in vivo metformin plasma profile of the formulation described in Example 2 and the in vivo metformin plasma profile of the commercially available metformin HCl product GLUCOPHAGE® under fasting conditions.

FIG. 5 depicts the in vivo metformin plasma profile of the sustained release product prepared in this Example under fasting conditions. FIG. 5 also shows the in vivo metformin plasma profile of the GLUCOPHAGE® product under fasting conditions.

Figure 6:
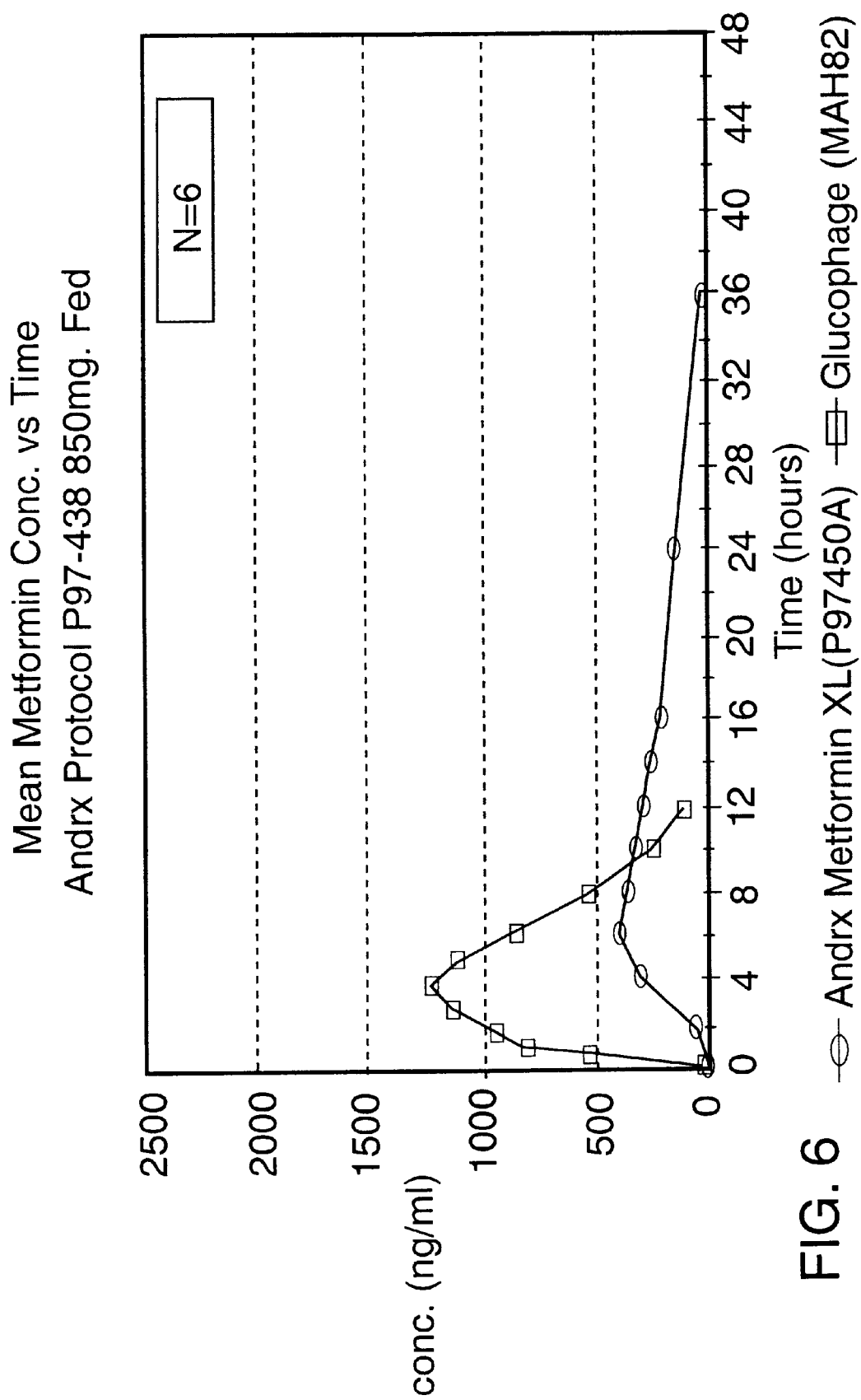
FIG. 6 is a graph depicting the in vivo metformin plasma profile of the formulation described in Example 2 and the in vivo metformin plasma profile of the commercially available metformin HCl product GLUCOPHAGE® under fed conditions.

FIG. 6 depicts the in vivo metformin plasma profile of the sustained release product prepared in this Example under fed conditions. FIG. 6 also shows the in vivo metformin plasma profile of the GLUCOPHAGE® product under fed conditions.

FIGS. 5 and 6 clearly show that the dosage forms prepared in accordance with the present invention exhibit consistent bioavailability under both fed and fasting conditions while the GLUOPHAGE® product's bioavailability decreases in the presence of food.

EXAMPLE 3

A controlled release tablet containing 850 mg of metformin HCl and having the same formula as in Example 2 is prepared as described in Example 2 except that an additional hole was drilled on the plain side of the coated tablet. The additional hole had a diameter of approximately 1 mm The resulting tablet is tested in simulated intestinal fluid (pH 7.5) and simulated gastric fluid (SGF) according to the procedure described in United States Pharmacopeia XXIII, Apparatus 2 @ 75 rpm and found to have the following release profile:

| TIME (hours) | % Released (SGF) | % Released (pH 7.5) |
|---|---|---|
| 2 | 13 | 14 |
| 4 | 27 | 28 |
| 8 | 50 | |
| 12 | 67 | 84 |
| 16 | 84 | 95 |
| 20 | 97 | 102 |

Figure 3:
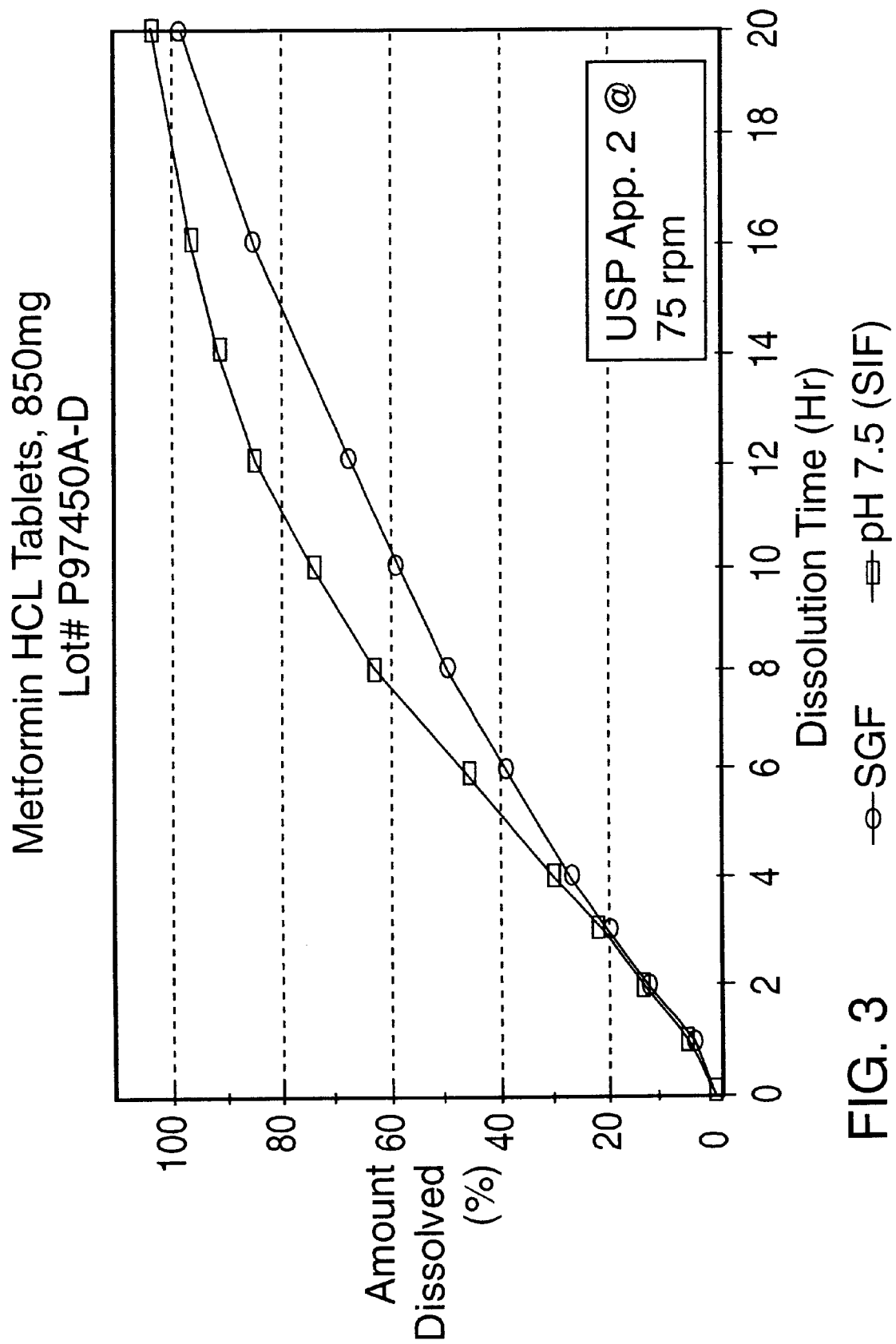
FIG. 3 is a graph which depicts the dissolution profile in simulated intestinal fluid (pH 7.5 phosphate buffer) and simulated gastric fluid (SGF) of the formulation described in Example 3 as tested according to the procedure described in United States Pharmacopeia XXIII, Apparatus 2 @ 75 rpm.

The release profile in pH 7.5 and SGF of the sustained release product prepared in this Example is shown in FIG. 3.

Figure 7:
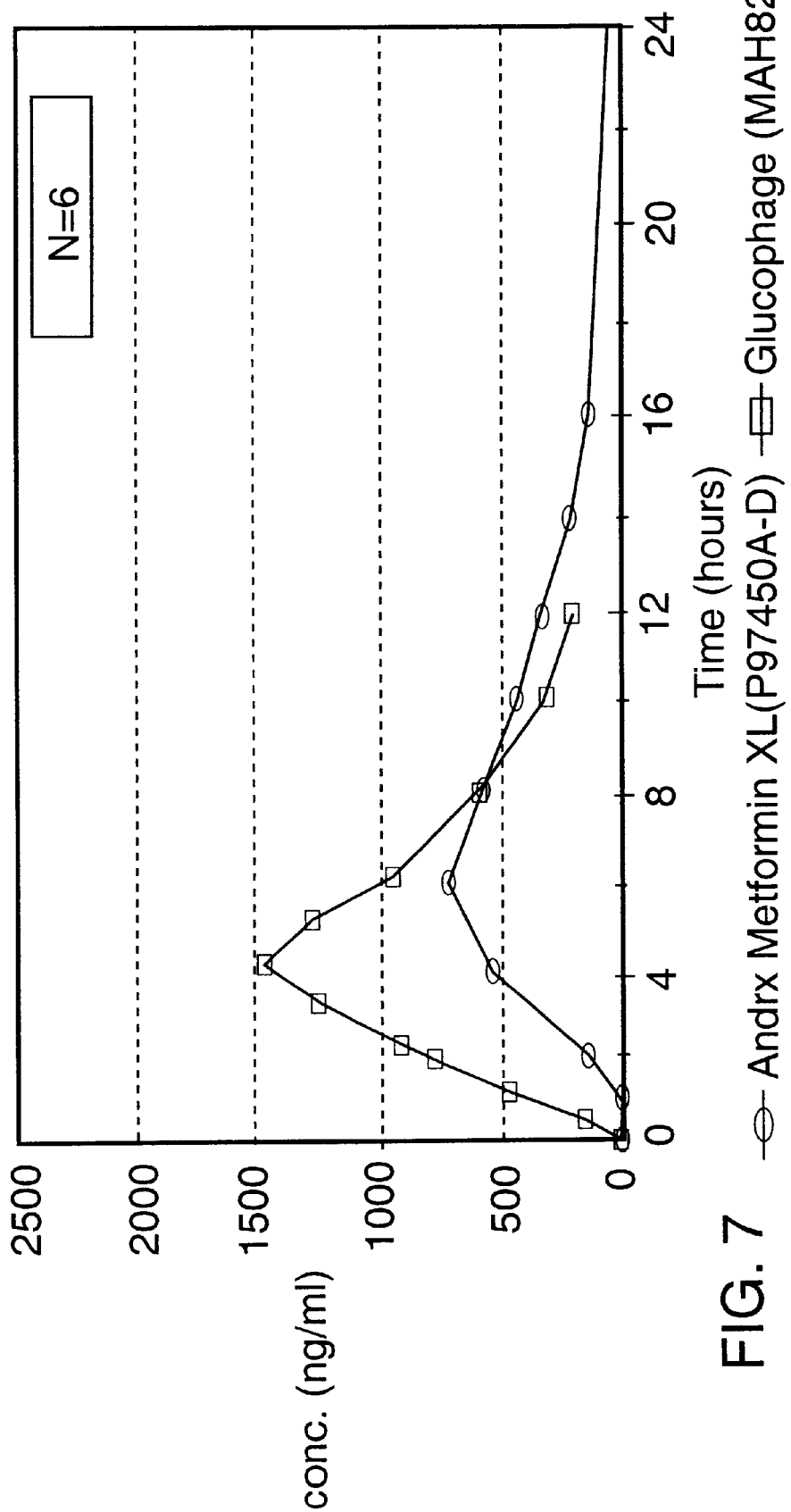
FIG. 7 is a graph depicting the in vivo metformin plasma profile of the formulation described in Example 3 and the in vivo metformin plasma profile of the commercially available metformin HCl product GLUCOPHAGE® under fed conditions (after breakfast).

FIG. 7 depicts the in vivo metformin plasma profile of the sustained release product prepared in this Example when administered shortly after breakfast. FIG. 7 also shows the in vivo metformin plasma profile of the GLUCOPHAGE® product administered shortly after breakfast.

Figure 8:
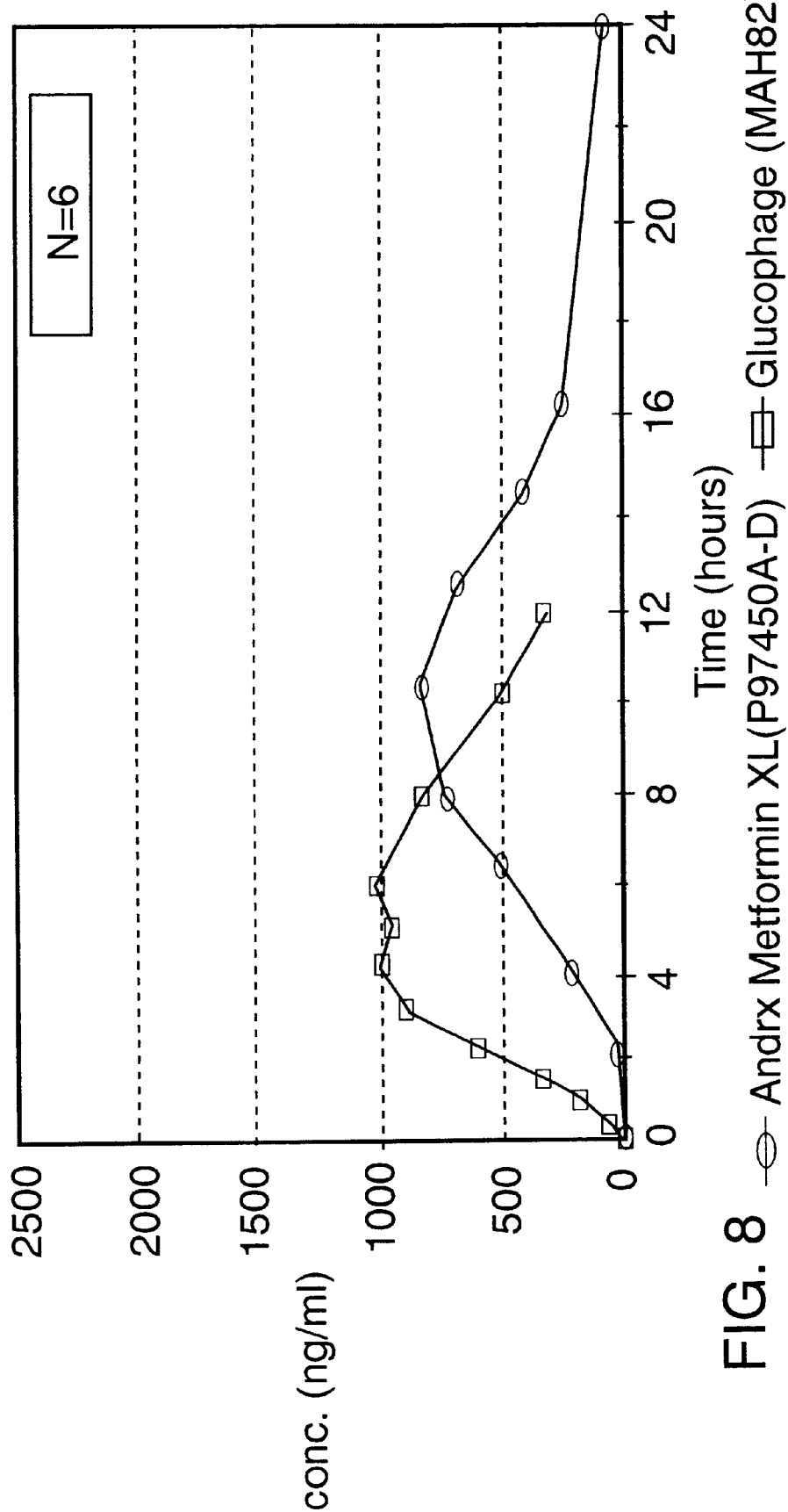
FIG. 8 is a graph depicting the in vivo metformin plasma profile of the formulation described in Example 3 and the in vivo metformin plasma profile of the commercially available metformin HCl product GLUCOPHAGE® under fed conditions (after dinner).

FIG. 8 depicts the in vivo metformin plasma profile of the sustained release product prepared in this Example when administered shortly after dinner. FIG. 8 also shows the in vivo metformin plasma profile of the GLUCOPHAGE® product administered shortly after dinner.

Table 1 is a summary of the bioavailability comparision data, test/reference ratio, shown in FIGS. 4–8 wherein the GLUCOPHAGE® product is the reference product in a two way crossover biostudy with n=6.

TABLE 1

| Formula | Figure | Study | AUC | Cmax | Tmax |
|---|---|---|---|---|---|
| Ex. 1 | 4 | Fasting | 0.202 | 0.12 | 2.15 |
| Ex. 2 | 5 | Fasting | 0.369 | 0.214 | 1.73 |
| Ex. 2 | 6 | Fed (bkft) | 0.628 | 0.305 | 1.94 |
| Ex. 3 | 7 | Fed (bkft) | 0.797 | 0.528 | 1.82 |
| Ex. 3 | 8 | Fed (dinner) | 0.850 | 0.751 | 2.00 | bkft = breakfast

The results reported in Table 1 and FIGS. 4–8 show that dosage forms prepared in accordance with the present invention exhibit an increase in the bioavailability of the antihyperglycemic drug in the presence of food, especially when taken with or shortly after the evening meal.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical tablet comprising:
    (a) a core comprising:
        (i) 50–98% of an antihyperglycemic drug;
        (ii) 0–40% of a binding agent; and
        (iii) 0–20% of an absorption enhancer;
    (b) a water soluble seal coat;
    (c) a semipermeable membrane coating covering said core wherein the membrane is permeable to the passage of water and biological fluids and is impermeable to the passage of the antihyperglycemic drug wherein said coating comprises 50–99% of a polymer; 0–40% of a flux enhancer and 0–25% of a plasticizer; and
    (d) at least one passageway in the semipermeable membrane for the release of the antihyperglycemic drug.

2. A controlled release pharmaceutical tablet as defined in claim 1 wherein the core consists essentially of:
    75–95% of the antihyperglycemic drug;
    3–15% of the binding agent; and
    2–10% of the absorption enhancer; and the coating comprises:
    75–95% of the polymer;
    2–20% of the flux enhancer; and
    2–15% of the plasticizer.

3. A controlled release pharmaceutical tablet as defined in claim 1 that exhibits the following dissolution profile when tested in a USP type 2 apparatus at 75 rpm in 900 ml of simulated intestinal fluid (pH 7.5 phosphate buffer) and at 37° C.:
    after 2 hours 0–25% of the drug is released;
    after 4 hours 10–45% of the drug is released;
    after 8 hours 30–90% of the drug is released;
    after 12 hours not less than 50% of the drug is released;
    after 16 hours not less than 60% of the drug is released; and after 20 hours not less than 70% of the drug is released.

4. A controlled release pharmaceutical tablet as defined in claim 1 that exhibits the following dissolution profile when tested in a USP type 2 apparatus at 75 rpm in 900 ml of simulated intestinal fluid (pH 7.5 phosphate buffer) and at 37° C.:
    after 2 hours 0–15% of the drug is released;
    after 4 hours 20–40% of the drug is released;
    after 8 hours 45–90% of the drug is released;
    after 12 hours not less than 60% of the drug is released;
    after 16 hours not less than 70% of the drug is released; and after 20 hours not less than 80% of the drug is released.

5. A controlled release pharmaceutical tablet as defined in claim 1 that is administered with or shortly after the evening meal.

6. A controlled release pharmaceutical tablet as defined in claim 1 wherein the binding agent is water soluble.

7. A controlled release pharmaceutical tablet as defined in claim 1 wherein the water soluble binding agent is polyvinyl pyrrolidone, hydroxypropyl cellulose, hydroxyethyl cellulose, waxes or mixtures thereof.

8. A controlled release pharmaceutical tablet as defined in claim 7 wherein the water soluble binding agent is polyvinyl pyrrolidone.

9. A controlled release pharmaceutical tablet as defined in claim 1 wherein the absorption enhancer is selected from the group consisting of fatty acids, surfactants, chelating agents, bile salts or mixtures thereof.

10. A controlled release pharmaceutical tablet as defined in claim 1 wherein the absorption enhancer is a fatty acid selected from the group consisting of capric acid, oleic acid or their monoglycerides.

11. A controlled release pharmaceutical tablet as defined in claim 1 wherein the absorption enhancer is a surfactant selected from the group consisting of sodium lauryl sulfate, sodium taurocholate and polysorbate 80.

12. A controlled release pharmaceutical tablet as defined in claim 1 wherein the absorption enhancer is a chelating agent selected from the group consisting of citric acid, phytic acid, ethylene diamine tetraacetic acid and ethylene glycol-bis(β-aminoethyl ether)-N,N,N,N-tetraacetic acid.

13. A controlled release pharmaceutical tablet as defined in claim 1 wherein the absorption enhancer is a bile salt.

14. A controlled release pharmaceutical tablet as defined in claim 1 wherein the absorption enhancer is sodium lauryl sulfate.

15. A controlled release pharmaceutical tablet as defined in claim 1 wherein the semipermeable membrane around the core is a water insoluble cellulose derivative.

16. A controlled release pharmaceutical tablet as defined in claim 15 wherein the water insoluble cellulose derivative in the membrane around the core is cellulose acetate.

17. A controlled release pharmaceutical tablet as defined in claim 1 wherein semipermeable membrane comprises a flux enhancer.

18. A controlled release pharmaceutical tablet as defined in claim 17 wherein the flux enhancer is sodium chloride, potassium chloride, sucrose, sorbitol, mannitol, polyethylene glycol, propylene glycol, hydroxypropyl cellulose, hydroxypropyl methycellulose, hydroxypropyl methycellulose phthalate, cellulose acetate phthalate, polyvinyl alcohols, methacrylic acid copolymers or mixtures thereof.

19. A controlled release pharmaceutical tablet as defined in claim 18 wherein the flux enhancer is polyethylene glycol with an average molecular weight between 380 and 420.

20. A controlled release pharmaceutical tablet as defined in claim 1 wherein the plasticizer is triacetin.

21. A controlled release pharmaceutical tablet as defined in claim 1 wherein at least two passageways are formed in the semipermeable membrane.

22. A controlled release pharmaceutical tablet as defined in claim 1 wherein peak plasma levels are obtained 8–12 hours after administration.

23. A controlled release tablet as defined in claim 1 wherein the antihyperglycemic drug is a biguanide.

24. A controlled release tablet as defined in claim 1 wherein the antihyperglycemic drug is metformin or a pharmaceutically acceptable salt thereof.

25. A controlled release antihyperglycemic tablet comprising:
(a) a core consisting essentially of:
(i) 50–98% of metformin or a pharmaceutically acceptable salt thereof;
(ii) 0–40% of a water soluble binding agent; and
(iii) 0–20% of an absorption enhancer;
(b) optionally a water soluble seal coat;
(c) a semipermeable membrane coating covering said core comprising:
(i) 50–99% of a polymer;
(ii) 0–40% of a flux enhancer; and
(iii) 0–25% of a plasticizer; and
(d) at least one passageway in the semipermeable membrane for the release of metformin.

26. A controlled release pharmaceutical tablet as defined in claim 25 wherein the core consists essentially of:
75–95% of the metformin of a pharmaceutically acceptable salt thereof;
3–15% of the binding agent; and
2–10% of the absorption enhancer;
and the coating comprises:
75–95% of the polymer;
2–20% of the flux enhancer; and
2–15% of the plasticizer; and
at least one passageway in the semipermeable membrane for the release of metformin.

27. A controlled release pharmaceutical tablet as defined in claim 25 that exhibits the following dissolution profile when tested in a USP type 2 apparatus at 75 rpm in 900 ml of simulated intestinal fluid (pH 7.5 phosphate buffer) and at 37° C.:
after 2 hours 0–25% of the drug is released;
after 4 hours 10–45% of the drug is released;
after 8 hours 30–90% of the drug is released;
after 12 hours not less than 50% of the drug is released;
after 16 hours not less than 60% of the drug is released; and after 20 hours not less than 70% of the drug is released.

28. A controlled release pharmaceutical tablet as defined in claim 25 that exhibits the following dissolution profile when tested in a USP type 2 apparatus at 75 rpm in 900 ml of simulated intestinal fluid (pH 7.5 phosphate buffer) and at 37° C.:
after 2 hours 0–15% of the drug is released;
after 4 hours 20–40% of the drug is released;
after 8 hours 45–90% of the drug is released;
after 12 hours not less than 60% of the drug is released;
after 16 hours not less than 70% of the drug is released; and after 20 hours not less than 80% of the drug is released.

29. A controlled release pharmaceutical tablet as defined in claim 25 that is administered with or shortly after the evening meal.

30. A controlled release pharmaceutical tablet as defined in claim 25 wherein the water soluble binding agent is polyvinyl pyrrolidone, hydroxypropyl cellulose, hydroxyethyl cellulose, waxes or mixtures thereof.

31. A controlled release pharmaceutical tablet as defined in claim 30 wherein the water soluble binding agent is polyvinyl pyrrolidone.

32. A controlled release pharmaceutical tablet as defined in claim 25 wherein the absorption enhancer is selected from the group consisting of fatty acids, surfactants, chelating agents, bile salts or mixtures thereof.

33. A controlled release pharmaceutical tablet as defined in claim 25 wherein the absorption enhancer is a fatty acid selected from the group consisting of capric acid, oleic acid or their monoglycerides.

34. A controlled release pharmaceutical tablet as defined in claim 25 wherein the absorption enhancer is a surfactant selected from the group consisting of sodium lauryl sulfate, sodium taurocholate and polysorbate 80.

35. A controlled release pharmaceutical tablet as defined in claim 25 wherein the absorption enhancer is a chelating agent selected from the group consisting of citric acid, phytic acid, ethylene diamine tetraacetic acid and ethylene glycol-bis(β-aminoethyl ether)-N,N,N,N-tetraacetic acid.

36. A controlled release pharmaceutical tablet as defined in claim 25 wherein the absorption enhancer is a bile salt.

37. A controlled release pharmaceutical tablet as defined in claim 25 wherein the absorption enhancer is sodium lauryl sulfate.

38. A controlled release pharmaceutical tablet as defined in claim 25 wherein the semipermeable membrane around the core is a water insoluble cellulose derivative.

39. A controlled release pharmaceutical tablet as defined in claim 25 wherein the water insoluble cellulose derivative in the membrane around the core is cellulose acetate.

40. A controlled release pharmaceutical tablet as defined in claim 25 wherein semipermeable membrane comprises a flux enhancer.

41. A controlled release pharmaceutical tablet as defined in claim 40 wherein the flux enhancer is sodium chloride, potassium chloride, sucrose, sorbitol, mannitol, polyethylene glycol, propylene glycol, hydroxypropyl cellulose, hydroxypropyl methycellulose, hydroxypropyl methycellulose phthalate, cellulose acetate phthalate, polyvinyl alcohols, methacrylic acid copolymers or mixtures thereof.

42. A controlled release pharmaceutical tablet as defined in claim 41 wherein the flux enhancer is polyethylene glycol with an average molecular weight between 380 and 420.

43. A controlled release pharmaceutical tablet as defined in claim 25 wherein the plasticizer is triacetin.

44. A controlled release pharmaceutical tablet as defined in claim 25 wherein at least two passageways are formed in the semipermeable membrane.

45. A controlled release pharmaceutical tablet as defined in claim 25 wherein peak plasma levels are obtained 8–12 hours after administration.

46. A controlled release pharmaceutical tablet as defined in claim 25 further comprising an effective amount of the metformin or pharmaceutically acceptable salt coated onto the semipermeable membrane or mixed into the semipermeable membrane to provide an immediate release of an effective amount of the metformin or pharmaceutically acceptable salt.

47. A controlled release tablet consisting of:
  (a) a core consisting essentially of:
    (i) 50–98% of metformin or a pharmaceutically acceptable salt thereof;
    (ii) 0–40% of a water soluble binding agent; and
    (iii) 0–20% of an absorption enhancer;
  (b) optionally a water soluble seal coat;
  (c) a semipermeable membrane coating covering said core consisting essentially of:
    (i) 50–99% of a polymer;
    (ii) 0–40% of a flux enhancer; and
    (iii) 0–25% of a plasticizer; and
  (e) at least one passageway in the semipermeable membrane for the release of metformin.

* * * * *